United States Patent [19]
Sridhar et al.

[11] Patent Number: 4,645,570
[45] Date of Patent: Feb. 24, 1987

[54] DISTILLATION OF HIGHER ALCOHOLS OF 6-20 CARBON ATOMS CONTAINING WATER AND METHANOL

[75] Inventors: Srinivasan Sridhar; Manfred Hartmann, both of Marl, Fed. Rep. of Germany

[73] Assignee: Huels Aktiengesellschaft, Marl, Fed. Rep. of Germany

[21] Appl. No.: 662,922

[22] Filed: Oct. 19, 1984

[30] Foreign Application Priority Data

Oct. 22, 1983 [DE] Fed. Rep. of Germany ....... 3338439

[51] Int. Cl.$^4$ .............................................. B01D 3/36
[52] U.S. Cl. ....................................... 203/73; 203/18; 203/63; 203/80; 203/99; 203/DIG. 19; 203/DIG. 23; 203/DIG. 25; 568/913
[58] Field of Search ............. 203/63, 73, 80, DIG. 23, 203/DIG. 25, 18, 99, DIG. 19; 568/913, 916, 918

[56] References Cited

U.S. PATENT DOCUMENTS

| | | | |
|---|---|---|---|
| 2,107,265 | 2/1938 | Archibald | 568/918 |
| 2,360,685 | 10/1944 | Petersen | 568/918 |
| 2,386,755 | 10/1945 | Spiers | 203/45 |
| 2,392,534 | 1/1946 | Keussler | 203/45 |
| 2,402,077 | 6/1946 | Patterson | 203/44 |
| 2,470,222 | 5/1949 | Patterson | 568/918 |
| 2,614,971 | 10/1952 | Burton | 203/18 |
| 3,442,770 | 5/1969 | Wentworth et al. | 203/18 |
| 4,342,627 | 8/1982 | Cane et al. | 568/916 |

FOREIGN PATENT DOCUMENTS

| | | | |
|---|---|---|---|
| 0108385 | 10/1958 | Pakistan | 568/916 |
| 1173217 | 12/1969 | United Kingdom | 568/917 |

OTHER PUBLICATIONS

The Chemical Abstract Reference CA 88 (1978): 52282e.
Buchold, "Natural Fats & Oils Route to Fatty Alcohols", Chemical Engineering; Feb. 21, 1983, pp. 42 & 43.

Primary Examiner—S. Leon Bashore
Assistant Examiner—V. Manoharan
Attorney, Agent, or Firm—Millen & White

[57] ABSTRACT

For the distillation of a stream consisting essentially of alcohols of 6-20 carbon atoms, water and methanol, the methanol is first separated from the homogeneous, aqueous solution as the overhead product by distillation under a head pressure of 500-1,000 mbar. The bottoms discharge is mechanically separated under normal pressure and at a temperature of 5°-95° C. in a phase separator to obtain a discrete water phase preferably containing at least two thirds of the feedstream water. The remaining organic phase is then transferred from the phase separator into a second distillation column and the organic phase is dewatered in the latter at 100-500 mbar. The head product from the second column is conducted to a second phase separator; the aqueous phase is separated therein at a temperature of 5°-95° C. and optionally returned into the first phase separator. The bottom product from the second distillation column is passed into a downstream distillation stage wherein the $C_6$ to $C_{20}$ alcohols are separated into fractions thereof.

20 Claims, 2 Drawing Figures

DISTILLATION OF HIGHER ALCOHOLS OF 6–20 CARBON ATOMS CONTAINING WATER AND METHANOL

BACKGROUND OF THE INVENTION

This invention relates to the distillation of fatty alcohols of 6–20 carbon atoms.

Fatty Alcohols can be produced from fatty acids in two different ways: by esterifying the acids to the methyl esters and subsequent hydrogenation to the alcohols, or by direct hydrogenation (Chem. Eng. 2/21/83, page 42). When two phases are formed, the aqueous phase is decanted off from the alcohol phase, and water dissolved in the alcohol phase is separated by distillation. The distillate comprises not only water but also volatile substances, such as hydrocarbons, esters, and the like, as well as methanol.

Esterification and simultaneous continuous separation of thus-formed water and of excess methanol can be conducted in a reaction column as well. Water can also be removed by azeotropic distillation with butanol (French Pat. No. 1,493,754 corresponding to British Pat. No. 1,173,217).

In a process for processing $C_1$ to $C_8$ alcohols prepared from synthesis gas (Russian Pat. No. 480,693) as well as hydrocarbons, the aqueous, homogeneous phase in a first step after hydrogenation, is freed of $C_1$ to $C_5$ alcohols and water by joint evaporation thereof.

Another process describes the separation of water and hydrocarbons in three distillation columns (CA 88 [1978]: 52282 e).

All of these processes have the common disadvantage that the distillation procedure to separate water is expensive.

Since the fatty alcohols are thermally unstable at temperatures above 250° C., the distillation must be conducted under a column pressure (at its head) of about 400 mbar or less. This requires both vacuum apparatus and the use of refrigeration. Furthermore, with relatively large proportions of dissolved water, i.e., equal to at least 5% by weight, the distillation is made considerably more difficult due to delays in boiling. The water separated by distillation contains—even after additional separation of methanol by distillation—volatile organic components. Therefore, before the water can be passed to waste, another chemical treatment is required. One process, for example, describes the cumbersome route of esterification, hydrogenation, amination, and rectification of the esters. Purification of the higher alcohols (for example the oxo synthesis) for the purpose of eliminating acids, esters, colorants, and the like, takes place by means of pure sodium and alkali washing (French Pat. No. 1,493,743 corresponding to British Pat. No. 1,173,217 and French Pat. No. 1,464,954 corresponding to U.S. Pat. No. 3,359,335).

Separation of the alcohols into the various desired fractions is accomplished by rectification.

Accordingly, the working-up operations used in the prior art are very cost-inefficient.

SUMMARY

An object of the invention, therefore, is to provide a working-up process wherein the distillation costs for the separation of water are reduced.

Another object is to provide a process wherein there is a reduction or elimination of the costly downstream working-up treatment for the wastewater so that this water can be passed to waste without appreciable chemical and/or biological processing.

Yet another objective is to provide a relatively simple, low cost system for the aforementioned separation of the higher alcohols.

Upon further study of the specification and appended claims, further objects and advantages of this invention will become apparent to those skilled in the art.

To attain these objects, there is provided a process wherein only methanol is separated overhead in a first distillation stage from a homogeneous feed mixture of methanol, water, and $C_{6-20}$ or $C_{8-20}$ alcohols. Distillation takes place at a head pressure of 500–1,000, preferably at 800–1,000 mbar. The water-containing bottoms product is passed to a phase separator where the water is separated mechanically as a discrete methanol-depleted aqueous phase from an organic alcohol phase containing water at 5°–95° C., preferably 50°–80° C. and under normal pressure. It has been found unexpectedly that the water can be discharged into the wastewater without any further purification. In general, the water contains only 500–1,000 ppm by weight of carbon, of this about 50–150 ppm by weight being methanol.

This second distillation for the dewatering of the alcohols is an azeotropic distillation with aid of low boiling alcohols such as octanol. Because octanol is also a product, it must be recovered from the azeotropic stream through an additional distillation. Also a lower boiling alcohol such as hexanol can be added as an azeotrope entrainer. Hexanol remains in the cycle on the top of the column for dewatering, whereas the octanol is available in anhydrous condition in the bottoms product.

Less than one-third (generally about 15 to 30% of the amount of water in the starting mixture remains in solution in the organic alcohol phase of the phase separation. This water is subsequently removed in a distillation column from the higher alcohols and any paraffins and any other intermediate boiling point compounds that may be present. The distillate again separates into two phases in a second phase separating tank. The aqueous phase is separated at a temperature of 5°–95° C., preferably 50°–80° C., and under normal pressure and optionally returned into the first separating tank. Also this aqueous phase of the distillate from the second column containing less than 2,000 ppm by weight of C, can be discharged into the wastewater. The fatty alcohols bottoms product from the second distillation column contains merely 100 ppm by weight of water. This dewatering step in the second column takes place at 100–500 mbar, preferably at 100–200 mbar.

This invention is for example particularly applicable to the separation of feedstreams of the following composition in percent by weight:

|  | general | preferred |
|---|---|---|
| Methanol | 20–50 | 25–35 |
| Water | 3–10 | 4–7 |
| Hydrocarbons | 0–1 | 0.1–0.5 |
| $C_{6/20}$ alcohols | 40–80 | 60–70 |

The feedstream must be homogeneous.

In a further downstream distillation arrangement, the fatty alcohols are separated into fractions in third and fourth distillation columns, for example into the mixtures $C_{6/10}$ or $C_{8/10}$; $C_{12/14}$; and $C_{16/18}$ or $C_{16/20}$ alcohols, respectively. In the third column, the $C_{6/10}$ or $C_{8/10}$ alcohols, respectively, are separated overhead as usual at 20–50 mbar, preferably 35–45 mbar head pressure. Separation of the $C_{12/14}$ and $C_{16/18}$ or $C_{16/20}$ fractions, respectively, from each other and from the high-boiling compounds takes place according to this invention in a fourth single column: The $C_{12}$ and $C_{14}$ alcohols leave the column overhead, and the $C_{16/18}$ or $C_{16/20}$ alcohols, respectively, are withdrawn from the bottom of the stripping section as a side stream in the vapor phase. The high boiling compounds are withdrawn from the sump. Distillation takes place at 5–40 mbar, preferably 10–20 mbar.

This distillation is conventional, already employed in the prior art. However the separation of the $C_{12}$–$C_{20}$ alcohols in three streams can made in one step according to the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1 (FIG. 1)

Figure 1:
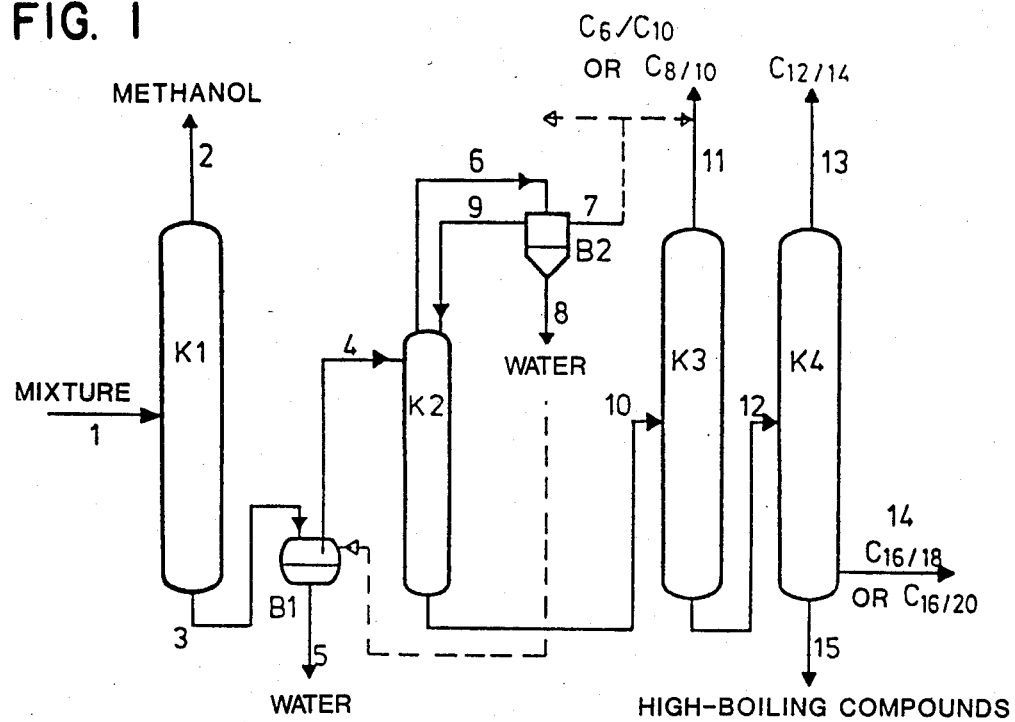
FIGS. 1 and 2 are schematic flowsheets of preferred embodiments of the invention which are explained in detail in the following examples, FIG. 1 differing from FIG. 2 by incorporating a fifth column K.5 to recover alcohol from the hydrocarbon phase 7 in the overhead in the second column K.2.

A homogeneous starting mixture of the following composition:

| | |
|---|---|
| methanol | 32% by weight |
| $C_{10+}$ hydrocarbons | 0.2% by weight |
| water | 5% by weight |
| $C_{8/18}$ alcohols | 62.3% by weight |
| and high-boiling compounds | 0.5% by weight | is introduced into column K1, having 50 practical plates, at the 10th plate and distilled continuously under 1,000 mbar and with a reflux ratio of 1. Methanol leaves the column overhead (stream 2) and contains only 100 ppm by weight of water. The bottom discharge (stream 3) is separated in separating tank B1 at room temperature into two phases. The bottom water phase with about 1,000 ppm by weight of C can be transferred out as wastewater. The top organic phase with about 4% by weight of dissolved water passes as stream 4 to the uppermost plate of a dewatering column K2 with 10 practical plates.

By distillation at 100 mbar, the dissolved water is removed azeotropically overhead together with octanol and hydrocarbons and separated as the water phase at room temperature in separating tank B2. At the beginning, the distillate streams from B2 are entirely introduced into the head of the column until a head temperature of 44° C. prevails. Only thereafter are the then-obtained quantities removed from B2 as streams 7 and 8, respectively. In the steady-state condition, the C8 alcohol is distributed between the azeotropically required proportion in the distillate and in the sump of K2. The water, with about 1,500 ppm by weight of C, can be directly removed, or it can be conducted into B1 and discharged as stream 5.

The bottoms discharge from K2 contains 100 ppm by weight of water and is free of methanol. This discharge passes as stream 10 to the 10th plate of column K3 with 20 practical plates. Separation of the $C_{8/10}$ alcohols overhead takes place under a head pressure of 20 mbar and with a reflux ratio of 2. The distillate is free of higher than $C_{10}$ alcohols, and the bottoms discharge is free of $C_{8/10}$ alcohols. The bottoms discharge from the K3 column is conducted to the 10th plate of the next column K4, containing 25 practical plates. Distillation is effected at 20 mbar and with a reflux ratio of 0.33. The thus-obtained distillate is constituted by the $C_{12/14}$ alcohols with 1% $C_{16/18}$ alcohols. The latter alcohols are withdrawn from the column as a secondary stream at the 2nd plate from the bottom. Stream 14 is free of $C_{12/14}$ alcohols and contains 1% of components boiling higher than the $C_{18}$ alcohol. The high-boiling compounds exit from the column as the bottoms discharge at a temperature of 240°–270° C., preferably 240°–250° C.

EXAMPLE 2 (FIG. 1)

Separation takes place as described in Example 1, but without removal of the organic phase from B2 (stream 7). Thus, only the proportion of hydrocarbons required for an azeotrope remains in the circulation of streams 6 and 9. The remainder is passed via stream 10 to stream 11 where it appears in the $C_{8/10}$ cut. In comparison, this remainder appeared in Example 1 in the $C_{8/10}$ cut via both streams 7 and 10. Furthermore, in Example 2, the proportion of water dissolved in the organic phase of B2 finds no access to stream 11.

EXAMPLE 3 (FIG. 1)

Separation takes place as in Example 2. At the beginning of distillation in K2, however, hexanol is added to the feed stream 4, namely in a ratio of 1/340 part by weight of hexanol per part of stream 4 (composition of starting mixture as in Example 1).

The feed is interrupted when the head temperature equals 44° C. if only a small amount of $C_{8+}$ alcohols is determined to exist in stream 9. The more readily boiling hexanol takes over the part of azeotropic agent for the hydrocarbons and the water and largely replaces the octanol. in the organic phase from separating tank B2. However, on account of a higher solubility displayed by hexanol, the carbon content in the aqueous phase is increased (about 3,000 ppm by weight). The aqueous phase is removed as in Example 1.

If hexanol already exists in the starting mixture, it can be separated, in part, after reaching a steady-state operation, together with the hydrocarbons.

In this case, stream 11—as contrasted to Example 2—is devoid of water as well as hydrocarbons.

EXAMPLE 4 (FIG. 2)

Figure 2:
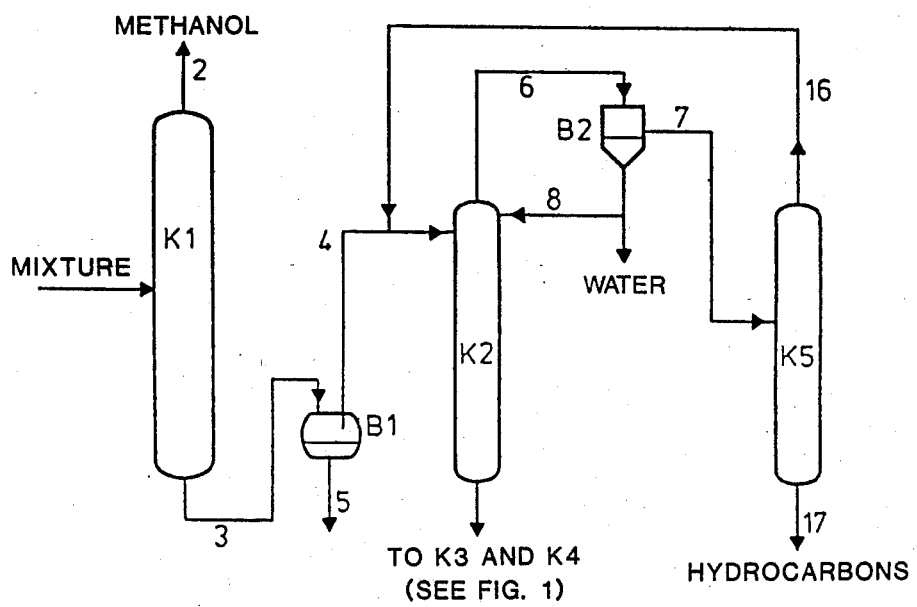

Withdrawal of the hydrocarbons via stream 7 (see FIG. 1) leads to a certain loss of alcohols. By the embodiment according to FIG. 2, the loss can be eliminated. The organic phase from B2 is distilled by being introduced into a further column K5, wherein the dissolved water, the alcohol, and the hydrocarbons are removed overhead and are introduced as stream 16 into K2. In case of a steady-state operation, the sump discharge contains only hydrocarbons (stream 17) and is free of alcohols. This mode of operation is especially advantageous if the starting mixture contains a relatively large proportion of hydrocarbons. Separation of the higher alcohols in K3 and K4 takes place in accordance with Example 1.

EXAMPLE 5 (FIG. 1)

The process of Example 1 is simplified by omitting phase separation in container B2 and recycling the entire distillate from K2 (stream 6) into tank B2. The water is merely separated as stream 5. The hydrocarbons appear in stream 11.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. In a distillation process for working up a homogeneous aqueous feedstream consisting essentially of alcohols of 6–20 carbon atoms, water and methanol, the improvement which comprises separating a stream consisting essentially of methanol alone as overhead from the homogeneous, aqueous solution in a first distillation column under a head pressure of 500–1,000 mbar; withdrawing a bottoms product from said first distillation column and passing said bottoms product to a first phase separator operating under atmospheric pressure wherein said bottoms product separates into an aqueous phase and an organic phase; mechanically separating the aqueous phase from the organic phase; passing the organic phase from the first phase separator into a second distillation column and dewatering the organic phase by azeotropic distillation at 100–500 mbar; passing the overhead product from said second distillation column into a second phase separator wherein an aqueous phase and an organic phase are formed; separating the aqueous phase from the second phase separator at a temperature of 5°–95° C.; withdrawing the bottoms product from the second distillation column and passing same into a downstream distillation stage wherein the $C_6$–$C_{20}$ alcohols are separated.

2. A process according to claim 1, wherein the methanol is separated under a head pressure of 800–1,000 mbar.

3. A process according to claim 1, wherein the second distillation column is operated under a head pressure of 100–200 mbar.

4. A process according to claim 2, wherein the second distillation column is operated under a head pressure of 100–200 mbar.

5. A process according to claim 1, the aqueous phase is separated at 50°–80° C. in at least one of the phase separators.

6. A process according to claim 4, wherein both phase separations are conducted at 50°–80° C.

7. A process according to claim 1, wherein at least about two thirds of the water in the aqueous feedstream is separated as the aqueous phase in the first phase separator.

8. A process according to claim 6, wherein at least about two thirds of the water in the aqueous feedstream is separated as the aqueous phase in the first phase separator.

9. A process according to claim 1, wherein hexanol is added to the feedstream in a sufficient quantity to function as an azeotropic agent in the second distillation column to form an azeotrope comprising water and hexanol.

10. A process according to claim 1, wherein the separation of the $C_6$–$C_{20}$ alcohols by distillation, comprises first separating the $C_6$–$C_{10}$ alcohols as the overhead product at 20–50 mbar head pressure in a $C_6$–$C_{10}$ column, passing resultant bottoms to a $C_{12}$–$C_{14}$ distillation column wherein the $C_{12\text{-}14}$ alcohols are obtained as the overhead product at 5–40 mbar head pressure, the $C_{16\text{-}20}$ alcohols are obtained as a vapor phase side stream near the bottom of the column, and higher boiling compounds are discharged as bottoms.

11. A process according to claim 10, wherein the $C_6$–$C_{10}$ column is operated at a head pressure of 35–45 mbar.

12. A process according to claim 10, wherein the $C_{12}$–$C_{14}$ column is operated at a head pressure of 10–20 mbar.

13. A process according to claim 11, wherein $C_{12}$–$C_{14}$ column is operated at a head pressure of 10–20 mbar.

14. A process according to claim 1, further comprising distilling the organic phase from the second phase separator to obtain a hydrocarbon cut, and withdrawing said hydrocarbon cut from the process.

15. A process according to claim 1 wherein the feedstream has the following composition in percent by weight: 20–50 methanol, 3–10 water, 0–1 hydrocarbons and 40–80 $C_6/C_{20}$ alcohols.

16. A process according to claim 1 wherein the feedstream has the following composition in percent by weight: 25–35 methanol, 4–7 water, 0.1–0.5 hydrocarbons and 60–70 $C_6/C_{20}$ alcohols.

17. A process according to claim 1, said aqueous phase in the first separator having 500–1000 ppm of C.

18. A process according to claim 1, wherein the alcohols in the feedstream are produced from fatty acids.

19. A process according to claim 1, wherein less than one-third of the water in the feedstream remains in the organic phase withdrawn from the first separator.

20. In a distillation process for working up a homogeneous aqueous feedstream consisting essentially of alcohols of 6–20 carbon atoms, water and methanol, the improvement which comprises separating a stream consisting essentially of methanol alone as overhead from the homogeneous, aqueous solution in a first distillation column under a head pressure of 500–1,000 mbar; withdrawing a bottoms product from said first distillation column and passing said bottoms product to a first phase separator operating under atmospheric pressure wherein said bottoms product separates into an aqueous phase and an organic phase; mechanically separating the aqueous phase from the organic phase; passing the organic phase from the first separator into a second distillation column and dewatering the organic phase by azeotropic distillation at 100–500 mbar, passing the overhead from said second distillation column into a second phase separator wherein an aqueous phase and an organic are formed; separating the aqueous phase from the second phase separator at a temperature of 5°–95° C.; and withdrawing from the second distillation column a bottoms product enriched in $C_6$–$C_{20}$ alcohols.

* * * * *